(12) United States Patent
Barbagelata et al.

(10) Patent No.: US 9,308,379 B2
(45) Date of Patent: Apr. 12, 2016

(54) REMOTE CAPABLE CARDIAC TREATMENT METHOD AND APPARATUS

(71) Applicants: N. Alejandro Barbagelata, League City, TX (US); James C. Mills, Houston, TX (US)

(72) Inventors: N. Alejandro Barbagelata, League City, TX (US); James C. Mills, Houston, TX (US)

(*) Notice: Subject to any disclaimer, the term of this patent is extended or adjusted under 35 U.S.C. 154(b) by 0 days.

(21) Appl. No.: 14/294,143

(22) Filed: Jun. 2, 2014

(65) Prior Publication Data

US 2015/0343226 A1    Dec. 3, 2015

(51) Int. Cl.
| | |
|---|---|
| *A61N 1/00* | (2006.01) |
| *A61N 1/372* | (2006.01) |
| *A61N 1/39* | (2006.01) |
| *A61N 1/362* | (2006.01) |
| *A61N 1/365* | (2006.01) |

(52) U.S. Cl.
CPC ............ *A61N 1/37282* (2013.01); *A61N 1/365* (2013.01); *A61N 1/3625* (2013.01); *A61N 1/3987* (2013.01)

(58) Field of Classification Search
CPC .................................................. A61N 1/3956
USPC ........................................................ 607/5, 7
See application file for complete search history.

(56) References Cited

U.S. PATENT DOCUMENTS

2013/0150909 A1* 6/2013 Azar et al. ......................... 607/7
2013/0190833 A1* 7/2013 Azar et al. ......................... 607/5

* cited by examiner

*Primary Examiner* — Nicole F Lavert
*Assistant Examiner* — Nadia A Mahmood
(74) *Attorney, Agent, or Firm* — Malcolm E. Whittaker; Whittaker Law Firm (57) ABSTRACT

A out-of-hospital cardiac treatment apparatus, comprising: a cardiac waveform monitor capable of sensing a physiological signal from a heart of a patient and wirelessly transmitting the sensed physiological signal to a remote medical provider, an electrical stimulator adapted to deliver a therapeutic dose of electrical energy to the heart of the patient, a medical provider transceiver adapted to receive the sensed physiological signal from the cardiac waveform monitor and also wirelessly transmit a command signal to control the electrical stimulator.

21 Claims, 8 Drawing Sheets

REMOTE CAPABLE CARDIAC TREATMENT METHOD AND APPARATUS

CROSS-REFERENCE TO RELATED APPLICATIONS

None

STATEMENT REGARDING FEDERALLY SPONSORED RESEARCH

Not Applicable.

TECHNICAL FIELD OF THE INVENTION

The present disclosure relates generally to systems, methods and apparatus for remote, also known as out-of-hospital or pre-hospital admission, and remote capable cardiac diagnosis and treatment. More particularly, the disclosure relates to remotely diagnosing and treating out-of-hospital life threatening arrhtymias such as ventricular tachycardia/fibrillation or severe bradyarrhytmias that may result in syncopal episode or cardiac arrest.

BACKGROUND

Life threatening arrhytmias such as Ventricular Tachycardia or Fibrillation and/or severe bradyarrhytmias are the main ethiology of out-of-hospital cardia arrest. The number one mortality ethiology in western world is cardiac disease. In particular, Myocardial infarction which is the medical term for a "heart attack," is a type of cardiac arrest. When a heart attack occurs, with a subsequent life threatening arrhytmias that alter the pumping action of the heart, the heart is disrupted such that it does not pump sufficient blood. Broadly speaking, the heart may either stop pumping or it may pump irregularly. In either situation, a trained medical professional can use a one-lead rhythm strip electrocardiograph to evaluate a patient's heart.

Figure 1A:
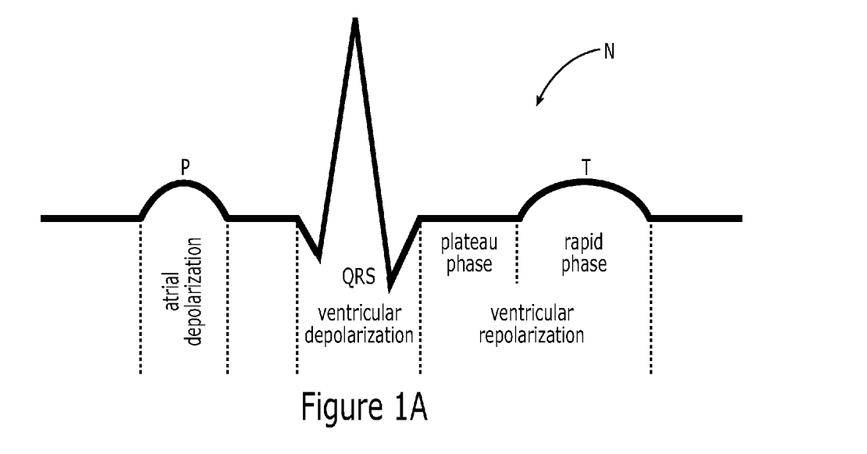
FIG. 1A is graphical view illustrating a characteristic waveform of an EKG of an example of one beat of a typical normal heart.
Figure 1B:
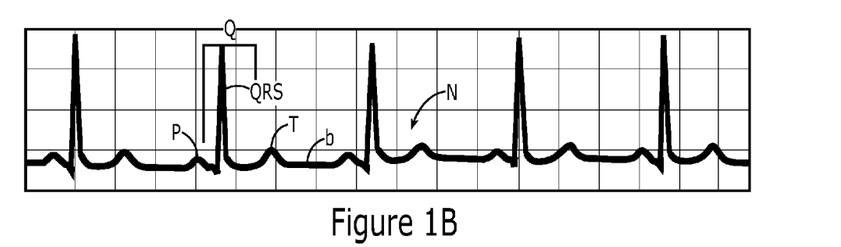
FIG. 1B is a graphical view illustrating an EKG of the rhythm of the normal heart.
Figure 2A:
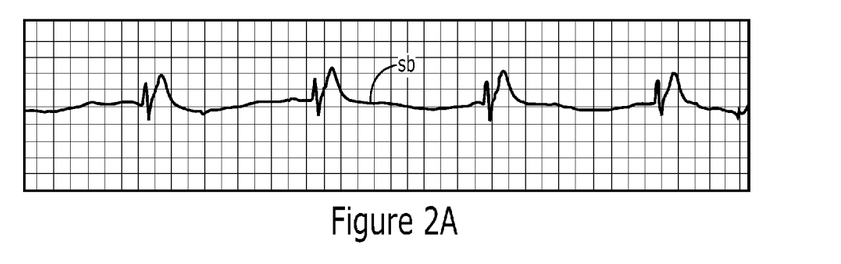
FIG. 2A is a graphical view illustrating a characteristic waveform of an EKG of an example of a severe bradyarrhytmia that requires stimulation, also known as pacing, by a pacemaker to regulate the heartbeat.
Figure 2B:
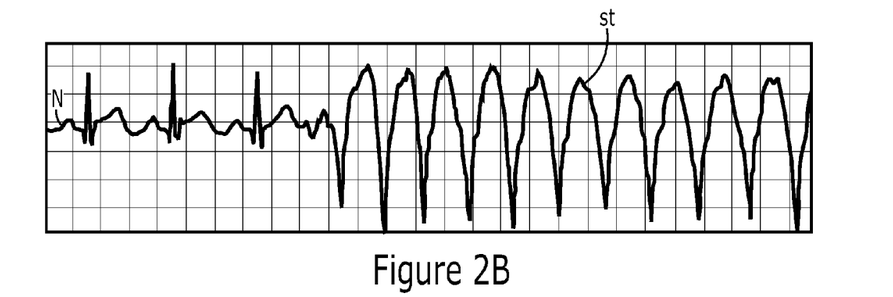
FIG. 2B is a graphical view illustrating a characteristic waveform of a severe tachycardia that requires stimulation, also known as pacing, by a pacemaker to regulate the heartbeat.
Figure 3A:
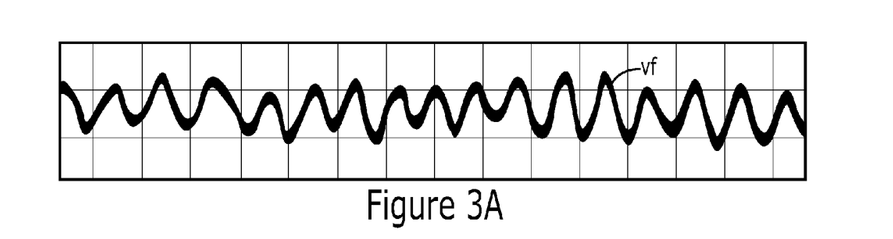
FIG. 3A is a graphical view illustrating a characteristic waveform of an EKG of a patient that has suffered a heart attack where the electrical activity of the patient's heart is irregular and potentially chaotic and generally referred to as ventricular flutter.

At its most basic, electrocardiography is a graphical interpretation of electrical activity of the heart over a period of time, as detected by electrodes attached to the surface of the skin and collected by a device external to the patient's body. An electrocardiogram (ECG or EKG are two abbreviations of the term "electrocardiogram) measures the electrical impulses generated by the polarization and de-polarization of cardiac tissue of the heart. The EKG translates these electrical impulses into a waveform. The waveform is used to determine the rate and regularity of the subject's heartbeats. Although to establish a diagnoses of a heart attack a 12-lead ECG is currently required, one lead is generally sufficient to detect significant arrhytmias that may require a treatment with a defibrillator or a pacemaker in an emergent setting. For example, the characteristic waveform of one beat of a normal heart is illustrated at FIG. 1A. FIG. 1B illustrates an EKG of a normal heart. FIG. 1B illustrates a cardiac cycle representing a P wave, a QRS complex, a T wave and a baseline b that follows until another P wave appears. FIG. 2A illustrates a characteristic waveform of a severe bradyarrhytmia sb that requires stimulation, also known as pacing, by a pacemaker to regulate the heartbeat. FIG. 2B illustrates a characteristic waveform of a severe tachycardia st. FIGS. 3A, illustrating ventriular flutter vf, and 3B, illustrating ventricular fibrilation vf', illustrate characteristic waveforms of a patient that has suffered a heart attack where the electrical activity of the patient's heart is irregular and potentially chaotic. In this situation, the patient's heart is beating, but the chambers are firing chaotically and insufficient blood is being pumped by the patient's heart. In this situation, a defibrillator is used to depolarize the heart muscle and terminate the dysrhythmia and allow the patient's body to reestablish a normal sinus rhythm.

At the present time, EKG data can be monitored and transmitted from the patient to a doctor's office or a health service center. For example, U.S. Pat. No. 8,509,882 discloses a personal monitoring device with a sensor assembly configured to sense physiological signals upon contact with the patient's skin. The sensor assembly produces electrical signals representing the sensed physiological signals. A converter assembly, integrated with and electrically contented to the sensor assembly, converts the electrical signals generated by the sensor assembly to a frequency modulated physiological audio signal having a carrier frequency in the range of from about 6 kHz to about 20 kHz.

Additional examples of patient monitoring are disclosed in U.S. Pat. No. 5,735,285 which discloses use of a hand-held device that converts a patient's EKG, also referred to as an ECG, into a frequency modulated audio signal that may then be analyzed by audio inputting via a telephone system to a selected hand-held computer device or to a designated doctor's office.

U.S. Patent Application Publication No. 2010/0113950 discloses an electronic device having a heart sensor including several leads for detecting a user's cardiac signals. The leads are coupled to interior surfaces of the electronic device housing to hide the sensor from view. Using detected signals, the electronic device can then identify and authenticate the user.

While all of the above are useful in diagnosing conditions of the patient's heart, they do not address the problem of treatment before hospital admission. Diagnosis can also be particularly problematic because the patient may be unstable or unconscious. It is known that early defibrillation/pacing and CPR is critical in out-of-hospital cardiac arrest. Typically, earlier treatment results in significantly higher long-term rates of survival and less acute damage to the patient's heart, and potentially, the patient's brain. Thus, it would be desirable to permit an emergent bystander to diagnose and provide treatment with the option of a medical professional to oversight the patient's management remotely. The present disclosure permits a bystander to diagnose and treat onsite and a medical professional to both remotely diagnose and remotely treat the patient. Phrased differently, an emergent bystander without a medical degree or training as a first-responder, also referred to as paramedic, could employ the presently disclosed device to diagnose and treat the patient with the option of a medical professional to oversight the patient's management remotely. It is believed that this presently disclosed device will be particularly useful for a family member to diagnose and treat the family member's cardiac situation when the family member is remote from a hospital or doctor's office.

SUMMARY OF THE INVENTION

A out-of-hospital cardiac treatment apparatus, comprising; a cardiac waveform monitor capable of sensing a physiological signal from a heart of a patient and wirelessly transmitting the sensed physiological signal to a remote medical provider; an electrical stimulator adapted to deliver a therapeutic dose of electrical energy to the heart of the patient; a medical provider transceiver adapted to receive the sensed physiological signal from the cardiac waveform monitor and also wirelessly transmit a command signal to control the electrical stimulator.

DETAILED DESCRIPTION OF THE INVENTION

Certain terms are used throughout the following description and claims to refer to particular components and configurations. As one skilled in the art will appreciate, the same component may be referred to by different names. This application does not intend to distinguish between components that differ in name, but not in function. In the following discussion, and in the claims, the terms "including" and "comprising" are used in an open-ended fashion, and thus should be interpreted to mean "including, but not limited to . . . ." Also, the term "couple" or "couples" is intended to mean either an indirect or direct electrical connection. Thus, if a first device couples to a second device, that connection may be through a direct electrical connection, or through an indirect electrical connection via other devices and connections.

The foregoing description of the figures is provided for the convenience of the reader. It should be understood, however, that the embodiments are not limited to the precise arrangements and figurations illustrated in the figures. Also, figures are not necessarily drawn to scale, and certain figures may be shown exaggerated in scale or in a generalized or schematic form, in the interest of clarity or conciseness. The same or similar elements may be marked with the same or similar reference numerals.

While various embodiments are described herein, it should be appreciated that the present disclosure encompasses many inventive concepts that may be embodied in a wide variety of contexts. The following detailed description of exemplary embodiments, read in conjunction with the accompanying drawings, is merely illustrative and is not to be taken as limiting the scope of the invention, as it would be impracticable to include all of the possible embodiments of the invention in this application. Upon reading this application, many alternative embodiments of the present disclosure will be apparent to a person of ordinary skill in the art. The scope of the invention is defined by the appended claims and equivalents thereof.

Illustrative embodiments of the disclosure are described below. In the interest of clarity, not all features of an actual implementation are described in this application. In the development of any such actual embodiment, numerous implement-specific decisions may need to be made to achieve design-specific goals, which may vary from one implementation to another. It will be appreciated that such a development, while possibly complex and time-consuming, would nevertheless be a routine undertaking for a person of ordinary skill in the art having the benefit of this application.

It is considered atypical when a heart attack occurs when a medical professional is present and can render treatment immediately. As discussed above, the short time after the heart attack occurs is referred to as the "golden" hour. This is not to say that treatment rendered more than an hour after the patient's heart attack is not valuable, only that the sooner treatment occurs, the more likely damage to the patient's heart, and potentially the brain, will be minimized, or potentially, avoided. Thus, it would be valuable to allow a medical professional to both remotely monitor, oversite and remotely treat the patient suffering from the heart attack or to allow an emergent bystander to monitor and treat the patient suffering from the heart attack.

Figure 4A:
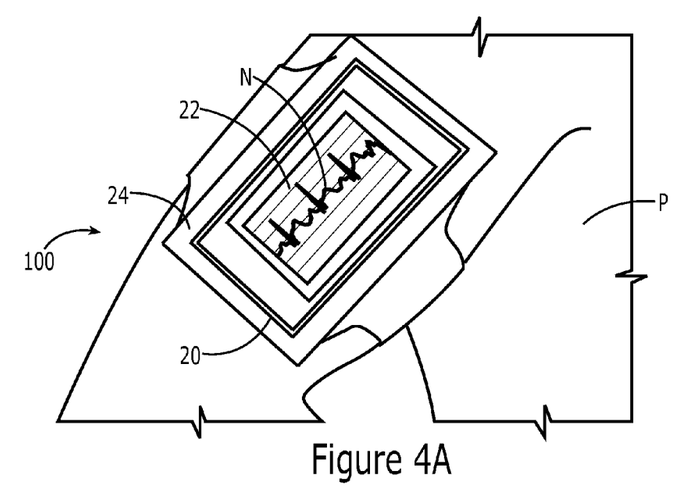
FIG. 4A is a schematic view illustrating a remote cardiac treatment apparatus.
Figure 4B:
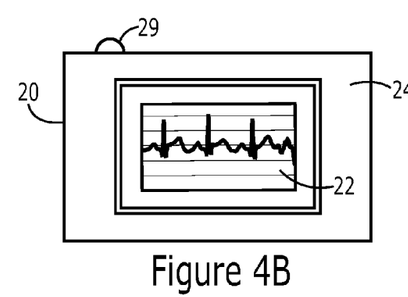
FIG. 4B is a front plan view illustrating a cardiac waveform monitor.
Figure 4C:
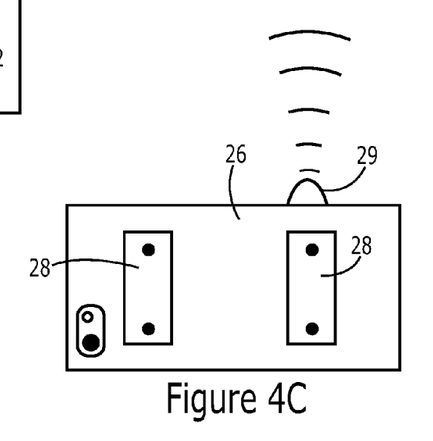
FIG. 4C is a back plan view illustrating the cardiac waveform monitor of FIG. 4B.

FIGS. 4A, 4B and 4C illustrate a remote cardiac treatment apparatus 100. A cardiac waveform monitor 20 is seen positioned on an arm of a patient P. Alternatively, the cardiac waveform monitor 20 can be positioned such that it contacts the patient's fingertips or chest. Because the cardiac waveform monitor 20 measures electrical impulses of the patient's heart, it should be positioned so that it can receive these electrical signals. Generally speaking, cardiac waveform monitor 20 performs best when it is positioned on the patient P's chest or fingertips. FIG. 4B illustrates a front plan view of the cardiac waveform monitor 20. Monitor 20 includes a screen 22 and case 24. FIG. 4C is a back plan view and illustrates attachment plate 26. Attachment plate 26 includes electrodes 28. Collectively, cardiac waveform monitor 20 may be thought of as a single-channel electrocardiogram. Preferably, screen 22 should display the electrocardiogram of the patient P and the patient's pulse rate. The preferred embodiment of the cardiac waveform monitor 20 is the AliveCor Heart Monitor sold by AliveCor, Inc., 30 Maiden Lane, $6^{th}$ Floor, San Francisco, Calif. 94108. According to Alive- Cor's website, www.alivecor.com, the AliveCor Heart Monitor is protected by "U.S. Pat. Nos. 8,301,232, 8,509,882 and [other] patents pending." U.S. Pat. Nos. 8,301,232 and 8,509,882 are incorporated by reference into this application as if set forth fully herein.

In addition, cardiac waveform monitor 20, illustrated in FIGS. 4A, 4B and 4C, may also be adapted to monitor respiration, heart beat, heart rate, electrocardiogram (EKG or ECG), electromyogram (EMG), electrooculogram (EOG), pulse oximetry, photoplethysmogram (PPG) and electroencephalogram (EEG). An EKG or ECG are measurements of the small electrical changes on the skin generated when the heart muscle depolarizes during each heartbeat. The output from a pair of electrodes 28 is sent to a patient transceiver 29. Small rises and falls in the voltage between two electrodes placed on either side of the heart can be processed to produce a graphical EKG representation on screen 22 thereby allowing the patient, emergent bystander and medical provider to view the EKG.

Nonlimiting examples of suitable cardiac waveform monitors 20 include, but are not limited to, miniature speakers, piezoelectric buzzers, and the like. The electrical impulses can be received by, for example, a microphone in a computing device such as a smartphone, personal digital assistant (PDA), tablet personal computer, pocket personal computer, notebook computer, desktop computer, server computer, and the like. In its preferred embodiment, cardiac waveform monitor is a smartphone with a touch screen, web browsing, Wi-fi and computing capability able to download and run mobile applications such as an "app" to monitor and wirelessly transmit cardiac data. A non-limiting example of an "app" or "application software" which can monitor cardiac function and wirelessly transmit cardiac data is Alivecor's "AliveECG app" for both the Apple's iPhone and Google's Android device.

Figure 5:
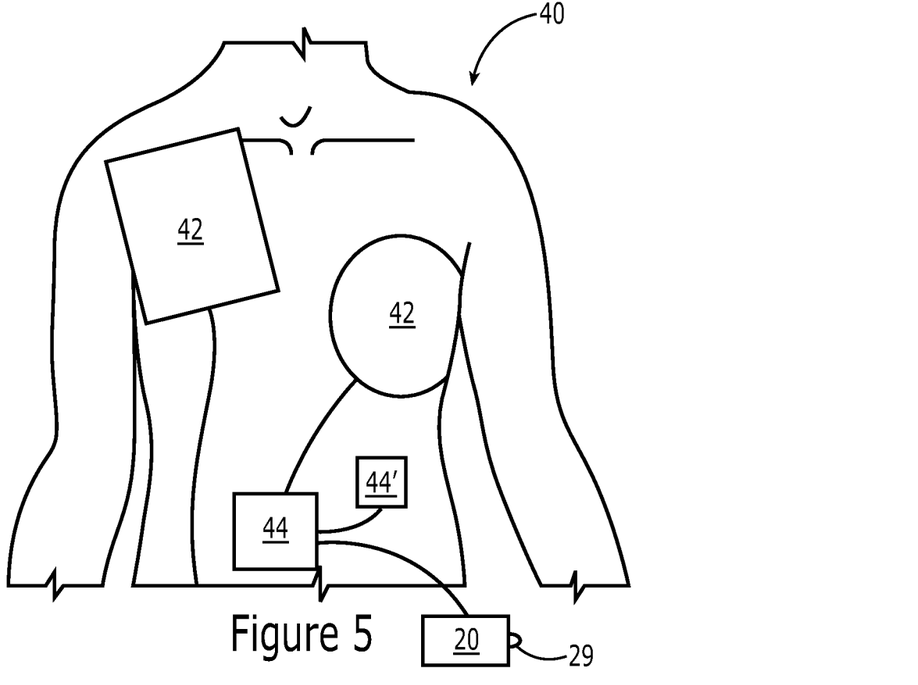
FIG. 5 is a schematic view illustrating typical positions for electrical stimulator pads on the patient's chest being treated for life threatening arrhtymias, such as ventricular tachycardia/fibrillation or severe bradyarrhytmias.

FIG. 5 is schematic view illustrating typical positions for the electrical stimulator's pads on the patient P's chest being treated for a heart attack. An electrical stimulator 40 includes pads 42. Pads 42 are placed on the chest of the patient P such that they can deliver a therapeutic dose of electrical energy to the heart of the patient P. As discussed above, this stimulation may take the form of electrical energy to pace or depolarize the patent P's heart. Energy source 44 provides the energy to treat patient P. Alternatively, energy source 44 could be supplemented by an external battery 44'. Because a cardiac waveform monitor 20 that is a smartphone with a fully charged Li-Po battery has 5.92 W hours of energy (21,312 Joules) it will likely provide the approximately 360 joules of energy required to defibrilate the patient. As such, an external battery 44' may not be needed. Of course, this assumes that the smartphone is fully charged. In addition, the ability of a battery to rapidly discharge is desirable. For example, a Lithium-Iron Phosphate Battery (LiFePO$_4$) discharges very rapidly. During defibrillation, the ability of the energy source to rapidly discharge and shock the patient's heart is desirable. In the situation where the cardiac waveform monitor 20 is "pacing" the patient's heart, the energy source should be able to provide a voltage of about 2.8 Volt(V).

Figure 6:
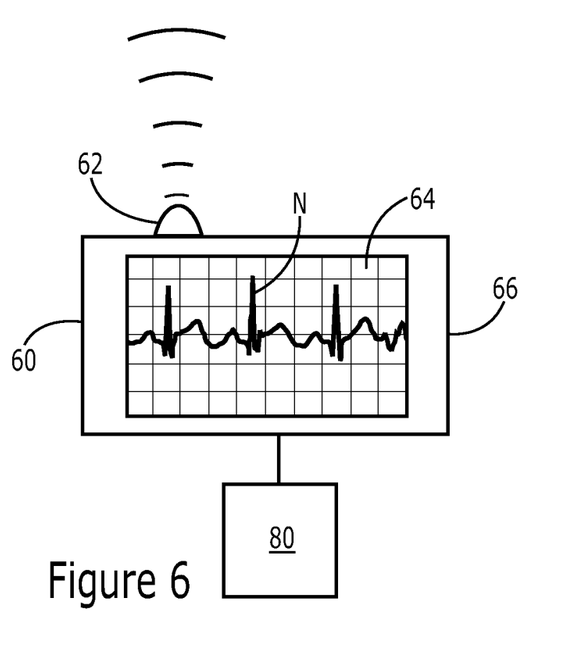
FIG. 6 is a schematic view illustrating a medical provider transceiver.

FIG. 6 illustrates a medical provider transceiver 60. The medical provider transceiver 60 includes provider transceiver 62, screen 64 and case 66. FIG. 6 illustrates that patient transceiver 29 has wirelessly communicated waveform N to provider transceiver 60 and waveform N is displayed on screen 64. Phrased differently, the waveform signal wirelessly communicated from transceiver 20 should be displayed on screen 64 of medical provider transceiver 60. In addition to being viewed on screen 64, the sensed physiological data can be stored on, one or more computing devices 80. Computing device 80 also permits a user to retrieve the stored sensed physiological data. In a preferred embodiment, a set of instructions, when executed by the one or more computing devices 80, can further cause the one or more computing devices 80 to calculate and display in real-time, a heart rate. In addition, demodulated digital EKG data can be processed to identify the occurrence of an arrhythmia. In such designs, the computing device 80 can include instructions to cause the computing device 80 to display a warning on a display screen 64 or emit an audible alert through a speaker upon detection of a suspected life theatening arrhytmia. Notwithstanding the forgoing, it should be understood that the patient transceiver 20 can transmit other waveforms and is not limited to transmitting only waveform N. The patient's sensed physiological data can be wirelessly networked via 3G or Wifi or transmitted via a network using USB LAN or any other means or wireless communication system.

Once received by medical provider transceiver 60, patient P's medical data can also be emailed or otherwise transmitted to the medical provider or viewed in real-time by the medical provider. Medical information such heart beat, heart rate, one lead rhythm strip electrocardiogram (EKG or ECG), can be provided to the medical provider through a smart phone or other computing device. Alternatively, the information could be stored on a computing device or serve and accessed by the medical provider.

Figure 3B:
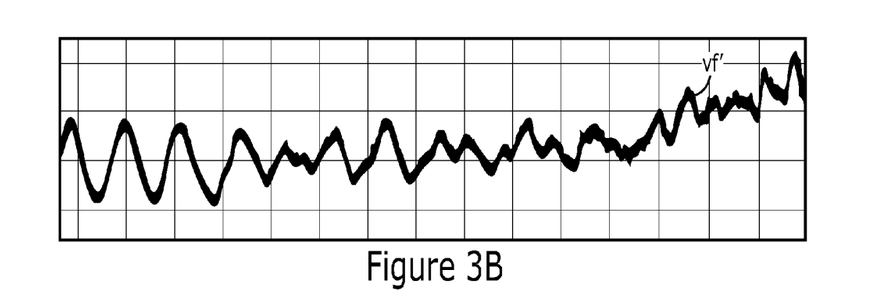
FIG. 3B is a graphical view illustrating a characteristic waveform of an EKG of a patient that has suffered a heart attack where the electrical activity of the patient's heart is irregular and potentially chaotic and generally referred to as ventricular fibrillation.
Figure 7A:
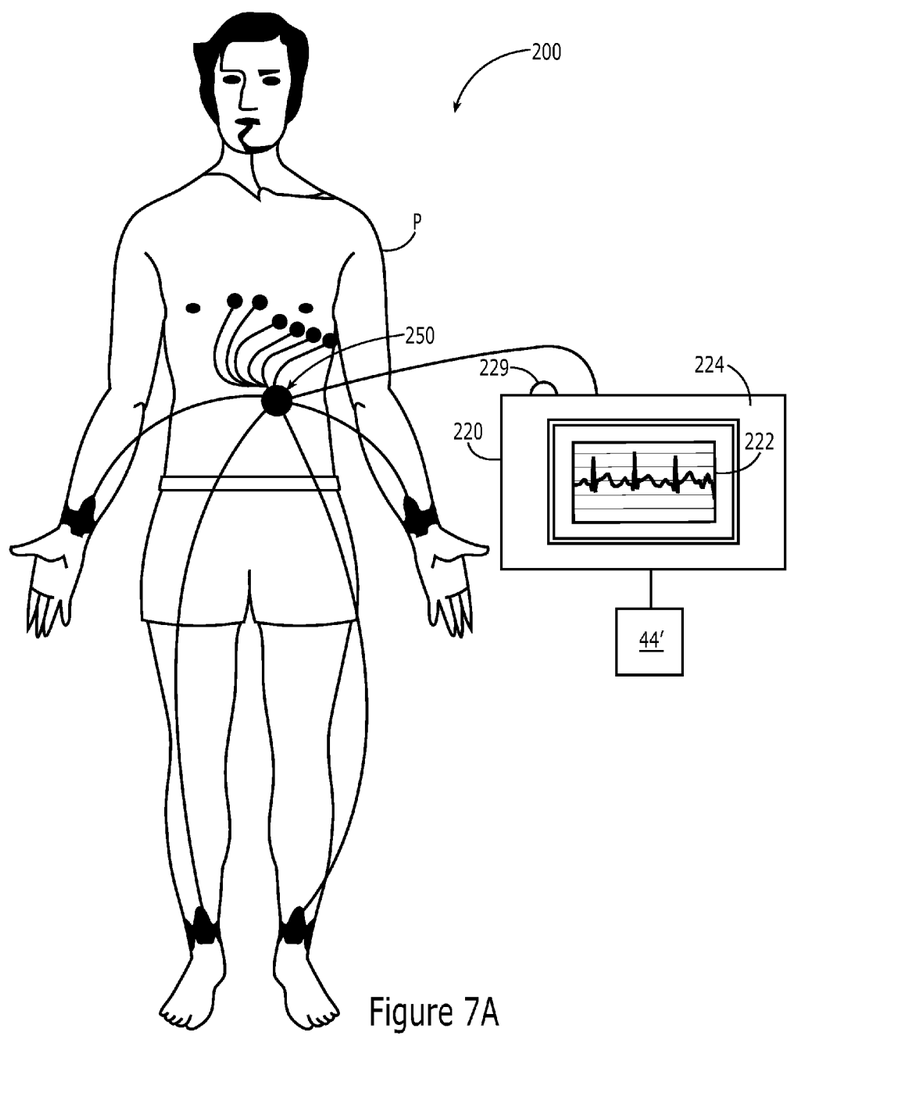
FIG. 7A is a schematic view of an alternative embodiment of a remote cardiac treatment apparatus illustrating use of a 12-lead EKG used in conjunction with a cardiac waveform monitor.

FIG. 7A illustrates a schematic view of an alternative embodiment of a remote cardiac treatment apparatus 200. The remote cardiac treatment apparatus 200 is illustrating as used in conjuction with a 12-lead EKG 250. It is known that a single lead EKG, such as the used in conjunction with a cardiac waveform monitor 220, is generally considered inadequate to diagnose ventricular flutter or ventricular fibrillation, illustrative examples of which are illustrated in FIGS. 3A and 3B. Thus, a user may elect to use 12-lead EKG 250, as opposed to single-lead EKG, for a more complete determination of the cardiac situation of patient P. Screen 222, of the cardiac waveform monitor 220, displays the 12 waveforms generated by a 12-lead EKG 250. Cardiac waveform monitor 220 is illustrated as having case 224 and transceiver 229. Cardiac waveform monitor 220 may also be positioned on the patient P's chest or fingertips.

Figure 7B:
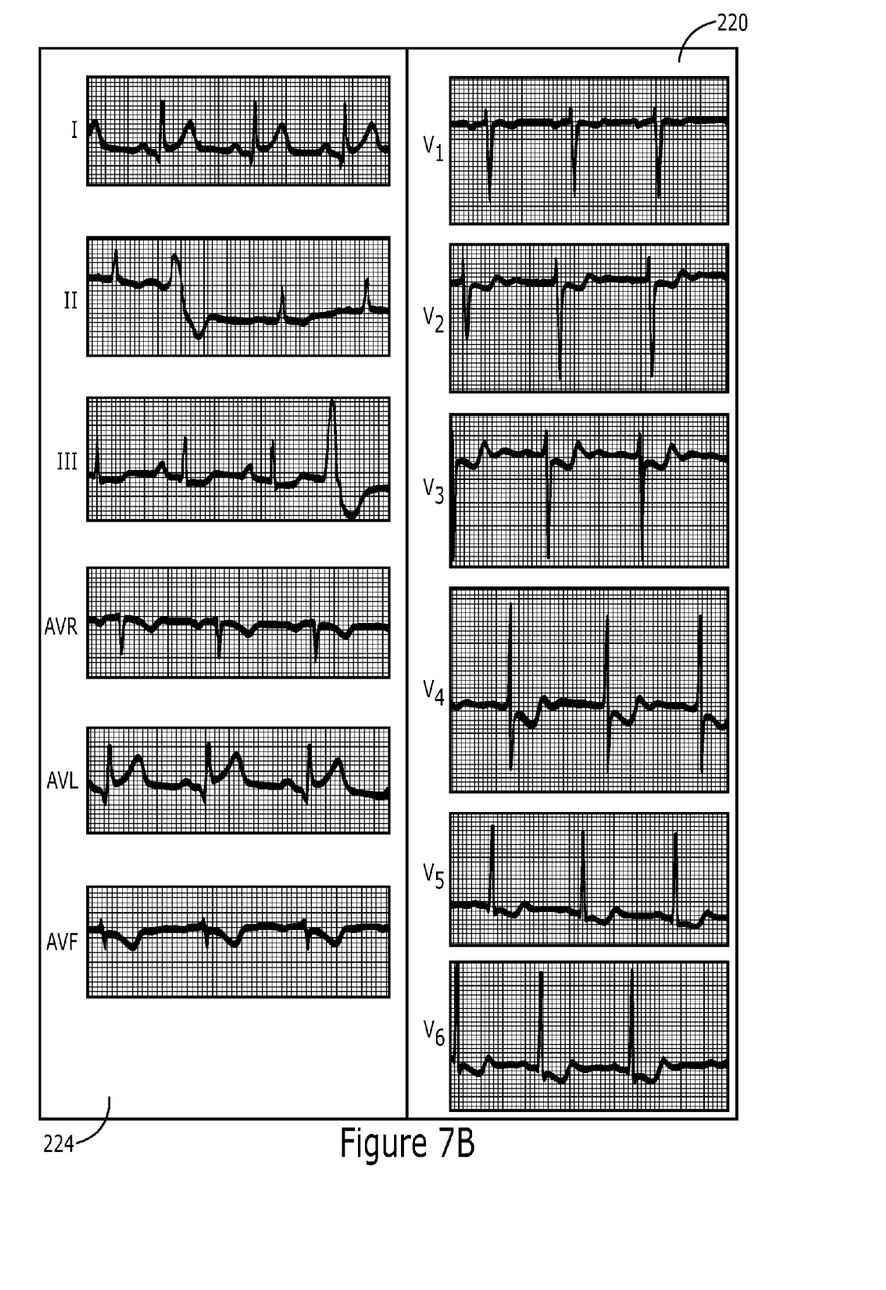
FIG. 7B illustrates a the twelve waveforms (I, II, III, AVR, AVL, AVF, $V_1$, $V_2$, $V_3$, $V_4$, $V_5$, $V_6$) of a 12-lead EKG.

FIG. 7B illustrates a 12-lead EKG 250 which displays 12 (twelve) waveforms (I, II, III, AVR, AVL, AVF, $V_1$, $V_2$, $V_3$, $V_4$, $V_5$, $V_6$), rather than the single wave form displayed by monitor 20 on screen 22. It should also be noted that leads are attached to the patient P at the locations illustrated in FIG. 7A. These are generally accepted positions for leads for 12-lead EKG 250 and, preferably, should not be varied. It is within the scope of the present invention that the number of EKG leads could vary.

Figure 8:
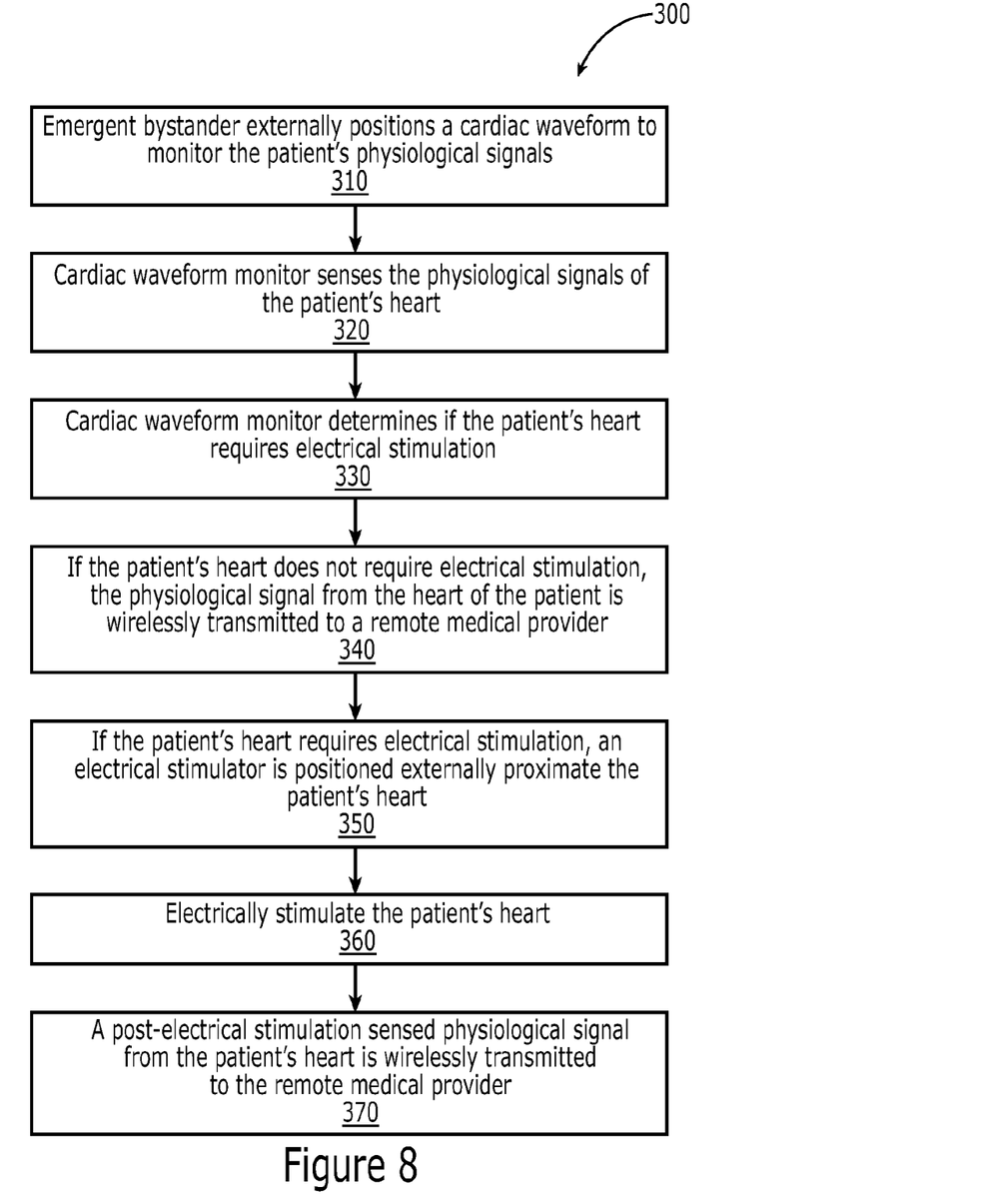
FIG. 8 is a block diagram of a method for an emergent bystander to diagnose and treat a heart attack.

FIG. 8 illustrates a method for an emergent bystander to diagnose and treat a heart attack when a patient is remote, out of hospital, from a medical provider 300. At 310, the emergent bystander externally positions a cardiac waveform to monitor a patient, the cardiac waveform monitor capable of sensing a physiological signal from a heart of the patient. At 320, the cardiac waveform monitor senses the physiological signal of the patient's heart. At 330, the cardiac waveform monitor determines if the patient's heart requires electrical stimulation. It should be understood that not all of the heart's conditions can be effectively treated by electrical stimulation. Thus, the electrical stimulation will not be delivered if the patient's heart rhythms are not shockable or paceable. At 340, if the patient's heart does not require electrical stimulation, the physiological signal from the heart of the patient is wirelessly transmitted to a remote medical provider. If the patient's heart requires electrical stimulation, an electrical stimulator is positioned externally proximate the patient's heart at 350. It should be understood that the electrical stimulator could be positioned before a treatment determination is made. However, it is probably preferable not to position the external electrical stimulator until after a treatment determination has been made to mitigate any risk of an unnecessary electrical stimulation of the patient. At 360, the patient's heart is electrically stimulated. At 370, a post-electrical stimulation sensed physiological signal from the patient's heart is wirelessly transmitted to a remote medical provider.

Figure 9:
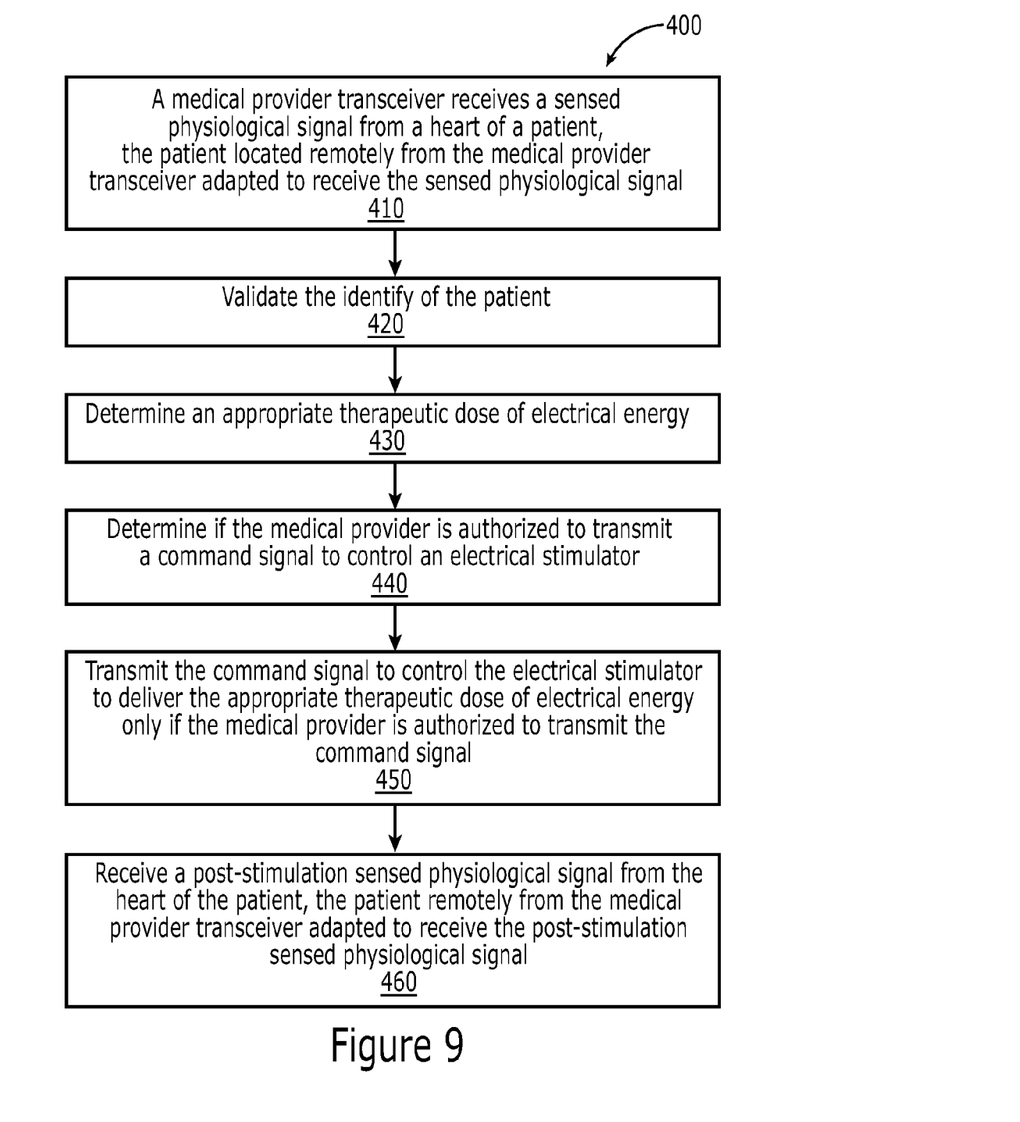
FIG. 9 is a block diagram of a method of remotely diagnosing and treating a heart attack.

FIG. 9 illustrates a method of remotely delivering cardiac treatment 400. At 410, the medical provider transceiver receives a sensed physiological signal from a heart of a patient, the patient is located remotely from a medical provider and the medical provider's transceiver is adapted to wirelessly receive the sensed physiological signal. At 420, the patient's identify is validated. This could be through an identifying code transmitted by the patient's transceiver or through biometric data. At 430, the medical provider determines an appropriate therapeutic dose of electrical energy, such as pacing or defibrillation. At 440, it is determined if a medical provider is authorized to transmit a command signal to control an electrical stimulator. The medical provider's authority to provide electrical stimulation to the patient can be validated by a biometric reader or entry of a password or the like. At 450, only if the medical provider's authority to provide electrical stimulation to the patient has been validated, the medical provider can transmit a command signal to control an electrical stimulator to deliver the appropriate therapeutic dose of electrical energy. It should be understood that not all of the heart's conditions can be effectively treated by electrical stimulation. Thus, the electrical stimulation will not be delivered if the patient's heart rhythms are not shockable or paceable. At 460, the medical provider receives a post-stimulation sensed physiological signal from a heart of a patient, the patient located remotely from a medical provider transceiver adapted to receive the post-stimulation sensed physiological signal. In this manner, the medical provider can determine if the electrical stimulation has achieved the desired result of appropriately restoring the patient's heart function.

Additional Information Concerning Electrical Stimulation

Modern defibrillators deliver current based on stored energy. Data demonstrates that 4 pad positions (anterolateral, anteroposterior, anterior-left infrascapular, and anterior-right-infrascapular are preferred. Ten studies indicated that larger pad/paddle size (8 to 12 cm diameter) lowers transthoracic impedance and that this is a preferred embodiment. To reduce transthoracic impedance, the defibrillator operator should use conductive materials. This is accomplished with the use of gel pads or electrode paste with paddles or through the use of self-adhesive pads Direct current defibrillators store an electrical charge and discharge it across two paddle electrodes in a damped, sinusoidal waveform. The shock terminates arrhythmias caused by re-entry by simultaneously depolarizing large portions of the atria or ventricles, thereby causing the re-entry circuits to extinguish.

Cardioversion refers to the termination of SVT or VT by delivery of a shock in synchrony with the QRS complex. When shocks are delivered to terminate VF, synchronization to the QRS complex is not necessary, and this process is referred to as defibrillation In the anteroapical configuration, one electrode is positioned to the right of the sternum at the level of the second intercostal space, and the second electrode is positioned at the midaxillary line, lateral to the apical impulse. In the anteroposterior configuration, an electrode is placed to the left of the sternum at the fourth intercostal space, and the second electrode is positioned posteriorly, to the left of the spine, at the same level as the anterior electrode. These two-electrode configurations result in similar success rates of cardioversion and defibrillation.

Important variables affecting the success of cardioversion or defibrillation are the shock waveform and shock strength. Defibrillators that deliver biphasic shocks are now clinically available and have a significantly higher success rate than conventional defibrillators. Other technique-dependent variables that maximize delivery of energy to the heart include firm paddle pressure, delivery of the shock during expiration, and repetitive shocks Asynchronous shocks may precipitate VF. Rarely, VF may occur even when shocks are synchronized to the QRS complex.

Biphasic Waveform Defibrillators—Data from both out-of-hospital and in-hospital studies indicate that lower-energy biphasic waveform shocks have equivalent or higher success for termination of VF than either MDS or MTE monophasic waveform shocks. However, the optimal energy for first-shock biphasic waveform defibrillation has not been determined. One study in which a pulsed biphasic waveform was used showed a first-shock success rate of 90%. There is no new evidence regarding the first-shock success rate with the rectilinear biphasic waveform since publication of the 2005 Guidelines. Several randomized and observational studies have shown that defibrillation with biphasic waveforms of relatively low energy (≤200 J) is safe and has equivalent or higher efficacy for termination of VF than monophasic waveform shocks of equivalent or higher energy.

Biphasic waveforms are safe and have equivalent or higher efficacy for termination of VF when compared with monophasic waveforms. In the absence of biphasic defibrillators, monophasic defibrillators are acceptable (Class IIb, LOE B)

For biphasic defibrillators, providers should use the manufacturer's recommended energy dose (eg, initial dose of 120 to 200 J) (Class I, LOE B). Higher energy might be biphasic waveforms of 200 to 400 J, 401-600 J or even higher.

Human studies have not demonstrated evidence of harm from any biphasic waveform defibrillation energy up to 360 J, with harm defined as elevated biomarker levels, ECG findings, and reduced ejection fraction.

A pacemaker typically delivers energy in a range from about 15 to 45 J when pacing the patient's heart.

We claim:

1. A method of remotely delivering cardiac treatment, comprising:
    sensing a physiological signal from a heart of a patient using a cardiac waveform monitor, the cardiac waveform monitor wirelessly transmitting the physiological signal of the heart of the patient to a remote medical provider;
    determining if the patient's heart requires a therapeutic dose of electrical stimulation, if the patient's heart does not require the therapeutic dose of electrical stimulation, wirelessly transmitting the patient's sensed physiological signal to the remote medical provider;

validating the identify of the patient;
determining an appropriate therapeutic dose of electrical stimulation;
determining if a medical provider is authorized to deliver the therapeutic dose of electrical stimulation;
transmitting a command signal to deliver the appropriate therapeutic dose of electrical stimulation only if the medical provider is authorized to transmit the command signal;
delivering the therapeutic dose of electrical stimulation; and
wirelessly transmitting the patient's post-stimulation sensed physiological signal to a remote medical provider.

2. The method of delivering cardiac treatment of claim 1, wherein the cardiac waveform monitor is a smartphone.

3. The method of delivering cardiac treatment of claim 2, wherein the smartphone is selected from the group consisting of: the smartphones sold under the trademarks—an APPLE IPHONE 5/5S®, a SAMSUNG S4® and a GOOGLE ANDROID®.

4. The method of delivering cardiac treatment of claim 1, further comprising providing an external battery.

5. The method of delivering cardiac treatment of claim 1, wherein the therapeutic dose of electrical stimulation paces the patient's heart.

6. The method of delivering cardiac treatment of claim 1, wherein the therapeutic dose of electrical stimulation defibrillates the patient's heart.

7. The method of delivering cardiac treatment of claim 1, wherein the therapeutic dose of electrical stimulation either paces or defibrillates the patient's heart.

8. The method of delivering cardiac treatment of claim 6, wherein the electrical stimulation delivers a biphasal waveform shock.

9. The method of cardiac treatment of claim 6, wherein the electrical stimulation delivers a monophasal waveform shock.

10. The method of cardiac treatment of claim 6, wherein the electrical stimulation delivers a biphasal waveform shock of more than 120 Joules and less than 200 Joules.

11. A method of delivering out-of-hospital cardiac treatment, comprising:
positioning a cardiac waveform monitor externally to a patient, the cardiac waveform monitor capable of sensing a physiological signal from the patient's heart;
sensing the physiological signal from the heart of the patient;
determining if the patient's heart requires a therapeutic dose of electrical stimulation, if the patient's heart requires the therapeutic dose of electrical stimulation, positioning an electrical stimulator externally to the patient and proximate to the patient's heart, if the patient's heart does not require the therapeutic dose of electrical stimulation, wirelessly transmitting the patient's sensed physiological signal to a remote medical provider;
delivering the therapeutic dose of electrical stimulation; and
wirelessly transmitting the patient's post-stimulation sensed physiological signal to the remote medical provider.

12. The method of delivering out-of-hospital cardiac treatment of claim 11, wherein the cardiac waveform monitor is a smartphone.

13. The method of delivering out-of hospital cardiac treatment of claim 12, wherein the smartphone is selected from the group consisting of: the smartphones sold under the trademarks—an APPLE IPHONE 5/5S®, a SAMSUNG S4® and a GOOGLE ANDROID®.

14. The method of delivering out-of-hospital cardiac treatment of claim 11, further comprising employing an external battery.

15. The method of delivering out-of-hospital cardiac treatment of claim 12, wherein the therapeutic dose of electrical energy paces the patient's heart.

16. The method of delivering out-of-hospital cardiac treatment of claim 11, wherein the therapeutic dose of electrical energy defibrillates the patient's heart.

17. The method of delivering out-of-hospital cardiac treatment of claim 11, wherein the therapeutic does of electrical energy either paces or defibrillates the patient's heart.

18. The method of delivering out-of-hospital cardiac treatment of claim 16, wherein the electrical stimulator delivers a biphasal waveform shock.

19. The method of delivering out-of-hospital cardiac treatment of claim 16, wherein the electrical stimulator delivers a monophasal waveform shock.

20. The method of delivering out-of-hospital cardiac treatment of claim 16, wherein the electrical stimulator delivers a biphasal waveform shock of less than 200 Joules.

21. The method of delivering out-of-hospital cardiac treatment of claim 16, wherein the electrical stimulator delivers a biphasal waveform shock of more than 120 Joules and less than 200 Joules.

* * * * *